US 6,571,794 B1

(12) United States Patent  
Hansen

(10) Patent No.: US 6,571,794 B1
(45) Date of Patent: Jun. 3, 2003

(54) MULTI-LUMEN HOSE FOR RESPIRATORS

(75) Inventor: Gary Hansen, Eden Prairie, MN (US)

(73) Assignee: Mallinckrodt, Inc., St. Louis, MO (US)

( * ) Notice: Subject to any disclaimer, the term of this patent is extended or adjusted under 35 U.S.C. 154(b) by 86 days.

(21) Appl. No.: 09/691,154

(22) Filed: Oct. 19, 2000

(51) Int. Cl.⁷ ................................................ A62B 7/00
(52) U.S. Cl. .................. 128/204.18; 138/111; 138/121; 138/127
(58) Field of Search ...................... 128/200.211, 204.18, 128/207.14, 207.18, 912; 138/111, 112, 116, 119, 121–127, 129–139, 144, 154, 177

(56) References Cited

U.S. PATENT DOCUMENTS

| 2,073,335 A | | 3/1937 | Connell | |
|---|---|---|---|---|
| 4,336,798 A | * | 6/1982 | Beran | 128/200.14 |
| 4,685,456 A | * | 8/1987 | Smart | 128/205.22 |
| 4,838,258 A | | 6/1989 | Dryden et al. | |
| 5,779,671 A | | 7/1998 | Ressemann et al. | |

FOREIGN PATENT DOCUMENTS

| DE | 199 54 724 A1 | 6/2001 | |
|---|---|---|---|
| EP | 0 672 430 A2 A3 | 9/1995 | |
| FR | 2 568 129 A2 | 1/1986 | |
| GB | 1156031 | 6/1969 | |
| GB | 2173274 | * 10/1986 | ............ 128/203.16 |
| WO | WO 0110489 A2 A3 | 2/2001 | |

* cited by examiner

Primary Examiner—Glenn K. Dawson
(74) Attorney, Agent, or Firm—Rothwell, Figg, Ernst & Manbeck, p.c.

(57) ABSTRACT

A respirator hose for connection between a ventilator and a breathing appliance during respiratory therapy includes a tubular body defining a first lumen for conveying a breathing gas from the ventilator, and a helical reinforcement member with a hollow core coiled around the tubular body to define a second lumen for conveying a second fluid in support of the respiratory therapy. The helical reinforcement member has a configuration to resist kinking and crushing of the tubular body that would close-off flow of the breathing gas. A fitting at one end of the hose can be keyed to simplify connections between the lumens and fluid communication ports of the ventilator.

14 Claims, 2 Drawing Sheets

MULTI-LUMEN HOSE FOR RESPIRATORS

BACKGROUND OF THE INVENTION

1. Field of the Invention

The present invention relates generally to the field of respiratory therapy and, more particularly, to respirator hoses used in conveying a breathing gas to a patient.

2. Description of the Background Art

Many forms of respiratory therapy involve use of a respirator hose to convey a breathing gas such as air to a patient. For such use, the respirator hose must be light enough to move about easily, but still be strong enough to resist crushing or kinking that would close-off flow of the breathing gas. A common method of fabricating respirator hoses is to wrap a thin, flexible plastic membrane about a helical or spiral support structure. The spiral support structure is typically formed of a hard metal wire or plastic.

In addition to respirator hoses, many forms of respiratory therapy require tubes running to or from the patient to convey other types of fluids. Some examples include tubes running from a breathing appliance such as a mask to a pressure sensor in the ventilator, tubes used to deliver water from a reservoir to a humidification device near a breathing appliance, and tubes used to deliver supplemental oxygen directly to a breathing appliance. With the growing complexity of respiratory therapy, many such situations exist or are envisioned for the future.

Multiple hoses and tubes running between the ventilator and the breathing appliance present the risk of tangling or inadvertent disconnection. Hooking up multiple hoses or tubes provides a potential source of error to the patient or nurse. Additionally, the presence of such extra hoses or tubes is an irritant for the patient, and may result in lack of compliance with the therapy.

SUMMARY OF THE INVENTION

Accordingly, it is an object of the present invention to provide an apparatus and method for conveying several fluids between a breathing appliance and a ventilator without the use of additional hoses or tubes.

A first aspect of the present invention is generally characterized in a respirator hose for connection between a ventilator and a breathing appliance during respiratory therapy. The respirator hose includes a tubular body defining a first lumen for conveying a breathing gas from the ventilator, and a helical reinforcement member with a hollow core coiled around the tubular body to resist kinking and crushing of the tubular body while defining a second lumen for conveying a second fluid in furtherance of the respiratory therapy. The tubular body is preferably pleated, with the helical reinforcement member being coiled around the tubular body between pleats. More than one helical reinforcement member with a hollow core can be coiled around the tubular body to define additional lumens. A fitting can be provided at one end of the hose to connect the lumens with corresponding fluid communication ports on the ventilator. If provided, such fitting is preferably keyed to ensure the proper connections are made.

Another aspect of the present invention is generally characterized in a method of administering respiratory therapy including the steps of connecting a hose having a tubular body and a helical reinforcement member coiled around the tubular body between a ventilator and a breathing appliance worn by a patient, conveying a breathing gas from the ventilator to the patient via a first lumen defined by the tubular body, and conveying a second fluid in support of the respiratory therapy via a second lumen defined by the helical reinforcement member. In a first preferred embodiment, the second fluid is a medicament and the step of conveying a second fluid includes delivering the medicament to the patient via the second lumen. In a second preferred embodiment, the second fluid is a humidifying liquid and the step of conveying a second fluid includes delivering the humidifying liquid to a humidifying device near the breathing appliance via the second lumen. In a third preferred embodiment, the second fluid is gas from the breathing appliance and the step of conveying a second fluid includes delivering gas from the breathing appliance to a pressure sensor at the ventilator via the second lumen. In a fourth preferred embodiment, the second fluid is supplemental oxygen and the step of conveying a second fluid includes delivering the supplemental oxygen to the breathing appliance via the second lumen.

Yet another aspect of the present invention is generally characterized in a breathing appliance having a hose connected thereto which includes a tubular member defining a first lumen in fluid communication with a gas inlet opening in the breathing appliance and a helical reinforcement member with a hollow core defining a second lumen in communication with a second opening in the breathing appliance.

The term "ventilator", as used herein, refers to any device of the type which generates a flow of breathing gas. The term "breathing appliance", as used herein, refers to a device, such as a mask, a nasal cannula, or a tracheostomy tube, that is worn by a patient to direct fluids from a hose into the patient's respiratory system. The term "respiratory therapy", as used herein, refers to any therapy or treatment wherein a breathing gas is delivered to a patient via a breathing appliance, including, by way of example, treatments for obstructive sleep apnea such as continuous positive airway pressure (CPAP) therapy and bilevel positive airway pressure (BiPAP) therapy.

The above and other features and advantages of the present invention will be further understood from the following description of the preferred embodiments thereof, taken in conjunction with the accompanying drawings in which like reference numerals are used to denote like parts.

DETAILED DESCRIPTION OF THE PREFERRED EMBODIMENTS

Figure 1:
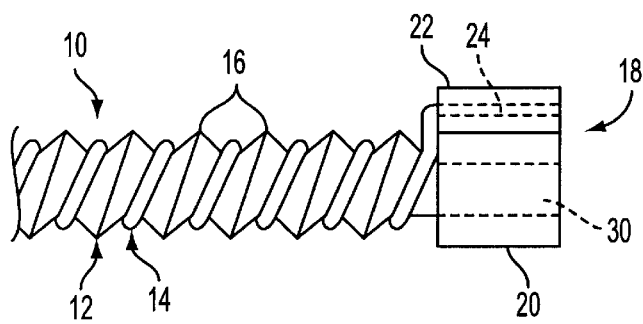
FIG. 1 is a fragmentary view of a distal portion of a respirator hose according to the present invention.
Figure 2:
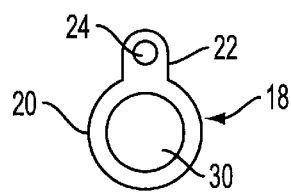
FIG. 2 is an end view of the respirator hose shown in FIG. 1.

FIGS. 1 and 2 show a gas delivery hose 10 according to the present invention. Hose 10 includes a pleated tubular body 12 reinforced by a helical reinforcement member 14 coiled around the tubular body between pleats 16. The hose terminates distally at a coupling or fitting 18 including a cuff 20 of hollow cylindrical configuration receiving the distal end of the hose body and a rib 22 extending laterally outward from one side of the cuff. The distal end of helical reinforcement member 14 extends away from hose body 12 to be received within a longitudinal passage 24 extending through rib 22. The proximal end of hose 10 can have any standard configuration for connecting with a breathing appliance such as a respirator mask, nasal cannula, or tracheostomy tube. For example, the proximal end of the hose can be fixed to the mask or terminate in a standard fitting configured to mate in a detachable manner with a gas inlet tube extending from the mask. Alternatively, the proximal end of hose can terminate in a fitting similar to that shown in FIGS. 1 and 2.

Figure 3:
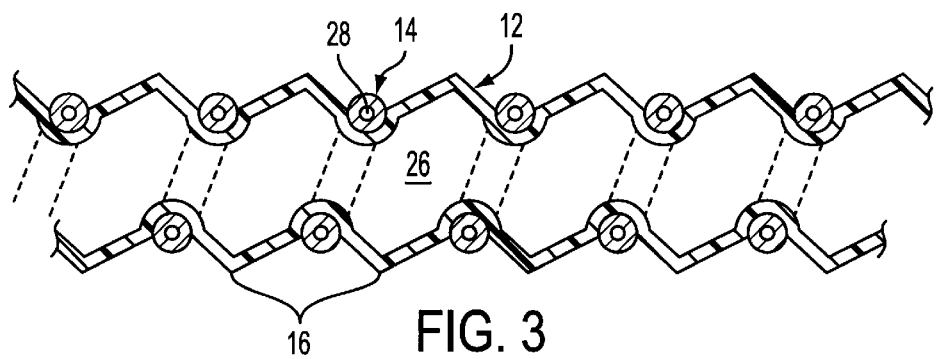
FIG. 3 is a cross-sectional view of the body of a respirator hose according to the present invention.

FIG. 3 is a sectional view illustrating further detail of gas delivery hose 10. In this view, it can be seen that hose body 12 is a pleated, tubular structure defining a first lumen 26 oriented along a longitudinal axis of the hose, and reinforcement member 14 is a hollow member defining a second lumen 28 that coils around the first lumen. Reinforcement member 14 is disposed in the lands between peaks of the pleats on an exterior surface of the hose body; however, the reinforcement member can be disposed within the wall of the hose body or on an interior surface of the hose body. If desired, the reinforcement member could be disposed along peaks of the pleats. Referring also to FIG. 1, it can be seen that the first lumen defined by hose body 12 is in fluid communication with the cylindrical opening or passage 30 defined by cuff 20, and the second lumen defined by the helical reinforcement member 14 is in fluid communication with the longitudinal passage 24 in rib 22.

Hose body 12 can be formed of any medically acceptable material commonly used in fabricating respirator hoses but is preferably formed of an elastomeric material that is highly flexible, impermeable to fluids, and tear resistant. It is also desirable for the hose body material to exhibit resistance to cracking under repeated flexure (e.g., greater than two million cycles) and chemical, ozone and UV resistance. Some examples of suitable materials include metallocene polyethylene, ethylene vinyl acetate, thermoplastic rubber, and Dupont Hytrel®. The dimensions of the hose body including wall thickness, diameter and length are the same as or similar to other commonly available respirator hoses. Generally, wall thickness is made as thin as possible to maximize flexibility and minimize weight. It is desirable but not necessary for the hose body to resist crushing and kinking to some degree. The ability of the hose body to resist crushing and kinking can be improved by use of a pleated structure or by forming the hose of an elastomeric material. Primary structural support for the hose body is provided by the helical reinforcement member.

Helical reinforcement member 14 can be formed of any medically acceptable material commonly used in fabricating helical reinforcement members for respirator hoses but is preferably formed of a metal or plastic material that is rigid enough to resist crushing and kinking without plastically deforming for wall thicknesses commonly used in respirator hoses. If desired, the reinforcement member can be made of the same material as the hose body so long as the dimensions of the reinforcement member are such that the reinforcement member has sufficient rigidity to resist crushing and kinking that can close-off flow through the hose. Advantages of using the same material are that virtually all such materials are compatible with the fluids likely to be conveyed as part of the respiratory therapy and that the hose body and reinforcement member can be formed as an integral, one-piece unit in a cost-effective manner by well-known manufacturing methods such as extrusion. When formed of different materials, the hose body and reinforcement member can be connected in any of the ways known to those of skill in the art of manufacturing respirator hoses. Some examples include the use of interference fits, adhesives, encapsulation, co-molding, and thermal welding.

The fitting at the distal end of the hose can be formed of any medically acceptable materially commonly used in fabricating fittings for respirator hoses but is preferably formed of a relatively hard silicone. The fitting can be connected to the rest of the hose in any of the ways known to those of skill in the art of manufacturing respirator hoses, including the examples listed in the above paragraph.

All hose materials should be able to survive high temperatures associated with sterilization (e.g., 160° F. in the case of pasteurization or 270° F. in the case of steam sterilization).

In use, respirator hose 10 is connected between a ventilator device and a breathing appliance to convey a breathing gas and possibly other fluids therebetween as part of some type of respiratory treatment or therapy. The respirator hose can be used in conjunction with any type of breathing appliance including, by way of example, masks, nasal cannula, and tracheostomy tubes. As mentioned above, the proximal end of the hose can be fixed to the breathing appliance or detachably coupled with the breathing appliance. The manner of attachment will be similar to that commonly used with existing respirator hoses, however, helical reinforcement member will also be attached to the breathing appliance as if it were a separate tube of the type the present invention is meant to eliminate. The respirator hose can be used in conjunction with any type of ventilator device but is particularly well suited for use in conjunction with a ventilator device having at least two fluid communication ports that are normally connected to the breathing appliance by a plurality of tubes and/or hoses. To avoid the possibility of reversing the connections, the ports are preferably arranged in a recess keyed to accept the fitting at the distal end of the hose in a particular orientation ensuring alignment of the passages in the fitting with the corresponding ports of the ventilator. For example, in FIG. 4, a ventilator 32 is shown having a first port 34 disposed within a cylindrical portion 36 of a recess and a second port 38 disposed within a rectangular or slotted portion 40 of the recess to function as a keyway. The cylindrical portion of the recess is configured to accept cuff 20 of fitting 18 and the slotted portion of the recess is configured to accept rib 22 extending from the cuff. Fitting 18 can only be inserted into the recess if rib 22 (i.e., the key) is aligned with slotted portion 40 (i.e., the keyway) of the recess. This orientation ensures alignment of first and second passages 30 and 24 with first and second ports, 34 and 38, respectively. A similar recessed port arrangement can be formed in the breathing appliance. Alternatively, the fitting may include a recess and the ventilator may include cooperatively configured male ports. As a further alternative, one of the ports may be recessed while the other port is formed as a male member.

Figure 4:
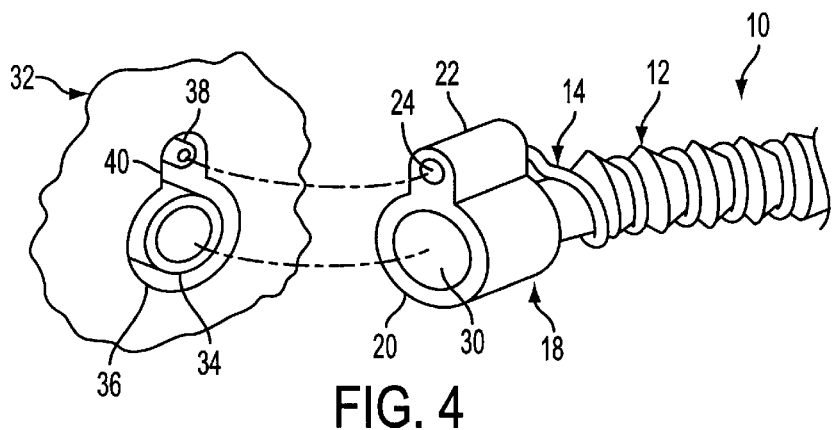
FIG. 4 shows how a respirator hose can be connected to a ventilator according to the present invention.

The hose shown in FIG. 4 is connected to ventilator 32 by inserting fitting 18 into the recess with rib 22 aligned with the slotted portion 40 at the top of the recess. Fitting 18 is keyed to fit in the recess in this orientation so that first and second passages 30 and 24 in the fitting are aligned to receive first and second ports, 34 and 38, of the ventilator. The first port 34 will typically deliver a breathing gas, such as air, at a positive pressure into the hose via the first passage 30 in the fitting. The breathing gas is conveyed to the breathing appliance through the first lumen defined by pleated hose body 12. The second port 38 can be connected to a pressure sensor in the ventilator, a source of water, a source of supplemental oxygen, or a source of a medicament such as an anesthetic or drug used in treating respiratory disorders such as sleep apnea. The lumen defined by the helical reinforcement member 14 establishes an unobstructed fluid path between the second port and the breathing appliance for accurately measuring gas pressure at the breathing appliance, delivering water to a humidification device near the breathing appliance, delivering supplemental oxygen to the breathing appliance, or delivering medicaments to the breathing appliance. The respirator hose can be disposed of after single patient use or sterilized for reuse.

Use of the respirator hose in the above manner facilitates complex respiratory therapy by allowing several fluids to be conveyed between a breathing appliance and a ventilator without the burden of managing multiple tubes and/or hoses. The respirator hose simplifies hook-up and improves patient comfort by eliminating additional tubes and/or hoses which would ordinarily need to be independently routed between the breathing appliance and the ventilator. Moreover, the respirator hose can be bent sharply without kinking like conventional respirator hoses due to the rigidity provided by the lumen-defining helical reinforcement member.

Figure 5:
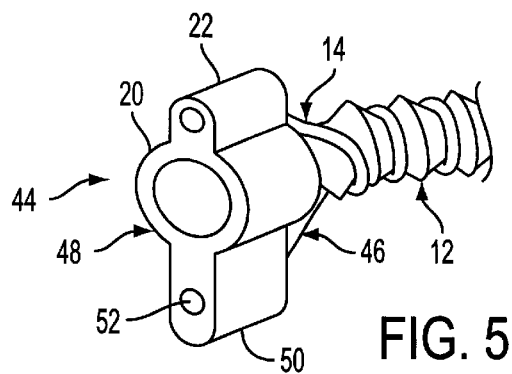
FIG. 5 shows another embodiment of a respirator hose according to the present invention.

The respirator hose of the present invention can have any number of lumens defined by helical reinforcement members. For example, in FIG. 5, another embodiment of a respirator hose 44 is shown wherein an additional lumen is defined by a second helical reinforcement member 46 coiled around the tubular body 12. Respirator hose 44 is similar to that described in conjunction with FIG. 1 but includes two helical reinforcement members 14 and 46 and a fitting 48 modified to couple the two helical reinforcement members in fluid communication with ports on a ventilator. The second helical reinforcement member 46 is identical to the first helical reinforcement member 14 but extends around the hose body between coils of the first helical reinforcement member. Fitting 48 at the distal end of the hose is identical to the fitting described in conjunction with FIG. 1 but includes a second rib 50 with a longitudinal passage 52 therein receiving the second reinforcement member. The second rib 50 is preferably diametrically opposed to the first rib 22 but can be located anywhere on cuff 20. Alternatively, a second passage can be formed through the first rib to receive the second reinforcement member so that a second rib is not required.

Figure 6:
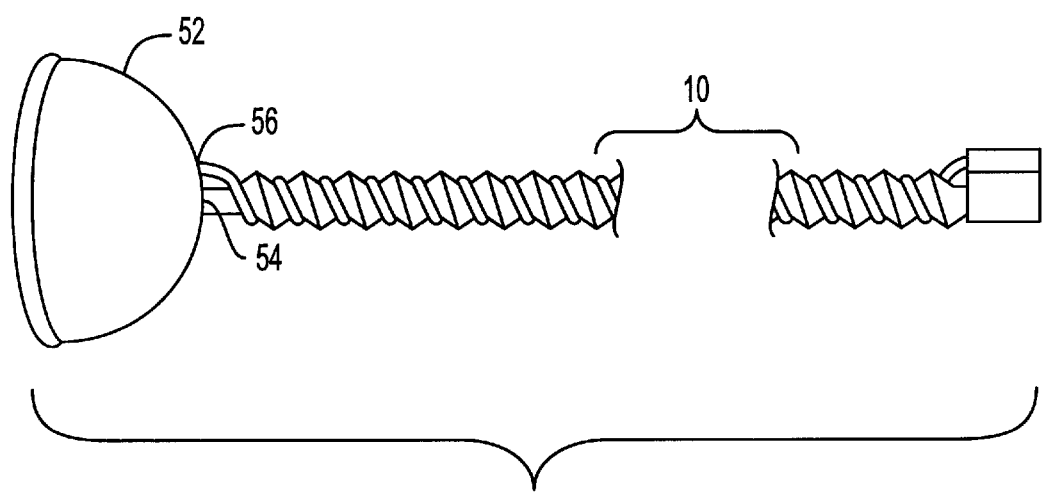
FIG. 6 shows a respirator hose connected to a breathing appliance according to the present invention.

FIG. 6 shows a respirator hose 10 connected to a breathing appliance 52. When connected as shown, the first lumen of the hose is in fluid communication with a gas inlet opening 54 in the breathing appliance and the second lumen of the hose is in fluid communication with a second opening 56 in the breathing appliance, either directly as shown or via a device (not shown), such as a humidifier, near the breathing appliance. If the hose includes additional lumens, each lumen can be connected to a corresponding opening in the breathing appliance.

While the invention has been described in detail above, the invention is not intended to be limited to the specific embodiments as described. It is evident that those skilled in the art may now make numerous uses and modifications of and departures from the specific embodiments described herein without departing from the inventive concepts. For example, the fittings can be keyed using grooves instead of, or in addition to, ribs. Ribs with passages formed therein can be combined with ribs having no passages formed therein. In addition, helical reinforcement members defining lumens can be combined with helical reinforcement members that do not define lumens.

What is claimed is:

1. A respirator hose for connection between a ventilator and a breathing appliance as part of a respiratory therapy, said hose comprising a tubular body defining a first lumen for conveying a breathing gas from the ventilator; and a helical reinforcement member coiled around said tubular body, said helical reinforcement member having a configuration to resist kinking and crushing of said tubular body that would close-off flow of the breathing gas and further having a hollow core defining a second lumen for conveying a second fluid in furtherance of the respiratory therapy;

wherein said tubular body is pleated and said helical reinforcement member is coiled around said tubular body between pleats.

2. A respirator hose as set forth in claim 1 wherein said helical reinforcement member is disposed along an exterior surface of said tubular body.

3. A respirator hose as set forth in claim 1 wherein said tubular body and said helical reinforcement member are both formed of an elastomeric material.

4. A respirator hose as set forth in claim 3 wherein said tubular body and said helical reinforcement member are formed as an integral one-piece member.

5. A respirator hose as set forth in claim 1 and further comprising a second helical reinforcement member coiled around said tubular body and defining a lumen for conveying a third fluid in support of the respiratory therapy.

6. A respirator hose as set forth in claim 1 and further comprising a fitting at one end of said hose having first and second passages in fluid communication with said respective first and second lumens.

7. A respirator hose as set forth in claim 6 wherein said fitting is keyed to ensure alignment of said first and second passages with corresponding fluid communication ports on the ventilator.

8. In combination, a respirator hose as set forth in claim 1 and a breathing appliance with first and second openings, said respirator hose and said breathing appliance being connected such that said first lumen communicates with said first opening and said second lumen communicates with said second opening.

9. A respirator hose for connection between a ventilator and a breathing appliance as part of a respiratory therapy, said hose comprising a tubular body defining a first lumen for conveying a breathing gas from the ventilator; and a helical reinforcement member coiled around said tubular body, said helical reinforcement member having a configuration to resist kinking and crushing of said tubular body that would close-off flow of the breathing gas and further having a hollow core defining a second lumen for conveying a second fluid in furtherance of the respiratory therapy;

wherein said tubular body is formed of an elastomeric material and said helical reinforcement member is formed of a metal material.

10. A method of administering respiratory therapy comprising the steps of connecting a hose having a tubular body and a helical reinforcement member coiled around the tubular body between a ventilator and a breathing appliance worn by a patient;

conveying a breathing gas from the ventilator to the patient via a first lumen defined by the tubular body;

conveying a second fluid in support of the respiratory therapy via a second lumen defined by the helical reinforcement member;

conveying a third fluid in support of the respiratory therapy via a third lumen defined by a second helical reinforcement member coiled around the tubular member.

11. A method as set forth in claim 10 wherein said second fluid is a medicament and said step of conveying a second fluid includes delivering the medicament to the patient via the second lumen.

12. A method as set forth in claim 10 wherein said second fluid is a humidifying liquid and said step of conveying a second fluid includes delivering the humidifying liquid to a humidifying device at the breathing appliance via the second lumen.

13. A method as set forth in claim 11 wherein said second fluid is gas from the breathing appliance and said step of conveying a second fluid includes delivering gas from the breathing appliance to a pressure sensor at the ventilator via the second lumen.

14. A method as set forth in claim 11 wherein said second fluid is supplemental oxygen and said step of conveying a second fluid includes delivering the supplemental oxygen to the breathing appliance via the second lumen.

* * * * *